United States Patent [19]
Meyerson et al.

[11] Patent Number: 5,179,947
[45] Date of Patent: Jan. 19, 1993

[54] ACCELERATION-SENSITIVE CARDIAC PACEMAKER AND METHOD OF OPERATION

[75] Inventors: Scott C. Meyerson, Mounds View; William J. Linder, Golden Valley; Keith R. Maile, New Brighton, all of Minn.

[73] Assignee: Cardiac Pacemakers, Inc., St. Paul, Minn.

[21] Appl. No.: 641,549

[22] Filed: Jan. 15, 1991

[51] Int. Cl.$^5$ ............................................. A61N 1/365
[52] U.S. Cl. ...................................... 128/419 PG
[58] Field of Search ................................. 128/419 PG

[56] References Cited

U.S. PATENT DOCUMENTS

| | | | |
|---|---|---|---|
| 4,428,378 | 1/1984 | Anderson et al. | 128/419 PG |
| 4,702,253 | 10/1987 | Nappholz et al. | |
| 4,886,064 | 12/1989 | Strandberg | 128/419 PG |
| 4,892,100 | 1/1990 | Schaldach | 128/419 PG |
| 4,940,052 | 7/1990 | Mann et al. | 128/419 PG |
| 5,027,813 | 7/1991 | Pederson et al. | 128/419 PG |

FOREIGN PATENT DOCUMENTS

| | | |
|---|---|---|
| 0331309 | 9/1989 | European Pat. Off. |
| 0361517 | 4/1990 | European Pat. Off. |
| 0392800 | 10/1990 | European Pat. Off. |
| 3226345 | 1/1989 | Fed. Rep. of Germany |
| 90/00478 | 8/1990 | World Int. Prop. O. |

OTHER PUBLICATIONS

Selective Vibration Sensing: A New Concept for Activity-Sensing Rate-Responsive Pacing, C. P. Lau et al.

Primary Examiner—William E. Kamm
Attorney, Agent, or Firm—Haugen and Nikolai

[57] ABSTRACT

An accelerometer based rate adaptive pacemaker generating an acceleration output signal corresponding to sensed acceleration of a patient's body. Apparatus for providing a sensor determined interval is coupled to the acceleration sensor and the sensor determined interval is proportional to the acceleration output signal. Apparatus for determining an actual pacing interval is coupled to an apparatus for determining a generated pacing interval. The generated pacing interval is a function of both the sensor determined interval and the actual pacing interval.

13 Claims, 5 Drawing Sheets

ACCELERATION-SENSITIVE CARDIAC PACEMAKER AND METHOD OF OPERATION

BACKGROUND OF THE INVENTION

I. Field of the Invention

This invention relates to signal processing and rate modulation in automatic cardiac pacers and, more particularly, to a rate adaptive pacer which provides pacing signals to the heart based on a root mean square approximation of band limited, low frequency, low level acceleration signals generated from body motion.

II. Description of the Prior Art

Activity sensing rate-responsive pacemakers have been developed which use body vibration during physical activity as an indicator of the need to alter pacing rate. One such prior art device is described in U.S. Pat. No. 4,428,378 to Anderson, et al., entitled "Rate Adaptive Pacer". The Anderson, et al. pacemaker operates by responding to a variety of mechanical forces both internal and external to a pacemaker patient. Because the Anderson, et al. pacemaker responds to forces applied to the patient's body, it must necessarily rely on the outside environment to provide a mass to generate the measured forces. Such masses as provided by the outside environment are subject to wide variations. Yet another deficiency of such prior art sensors is that they can measure only changes in pressure, not constant pressure. The present invention provides an activity sensing rate-responsive pacemaker including an accelerometer which contains a captive, well defined, constant reference mass.

Prior art rate adaptive pacemakers which are dependent on mechanical force sensors have been found to be relatively insensitive to different levels of exertion, particularly with respect to providing appropriate rate changes in response to a patient ascending stairs and walking up inclines. Such pacemakers are also susceptible to the effects of extraneous vibration such as that encountered in various forms of transport. One such study is reported by C.P. Lau, et al. in an article entitled "Selective Vibration Sensing: A New Concept for Activity—Sensing Rate-Responsive Pacing," P. 1299, PACE. Vol. II, Sep. 1988.

SUMMARY OF THE INVENTION

An accelerometer based rate adaptive pacemaker is provided. Means for sensing acceleration is included wherein the acceleration sensing means provides an acceleration output signal corresponding to the sensed acceleration. Means for a sensor determined interval is coupled to the acceleration sensing means wherein the sensor determined interval is proportional to the acceleration output signal. Means for determining an actual pacing interval provides the actual pacing interval to a means for determining a pacing rate. The pacing rate means is also coupled to the sensor determined interval means. The pacing rate is a function of both the sensor determined interval and the actual pacing interval.

In one aspect of the invention, the programmed pacing interval is decreased if the actual pacing interval exceeds the sensor determined interval.

In another aspect of the invention, a root mean square (RMS) approximation is applied to a sensor output to yield a sensor rectified average value which is used for pacing rate modulation.

In yet another aspect of the invention, analog means are provided for amplifying and band limiting a low frequency, low level accelerometer signal with very low noise.

In still another aspect of the invention, a method is provided for converting signal energy into a pacing rate.

Other objects, features and advantages of the present invention will become apparent to those skilled in the art through the Description of the Preferred Embodiment, Claims, and drawings herein wherein like numerals refer to like elements.

DESCRIPTION OF THE PREFERRED EMBODIMENT

Figure 1:
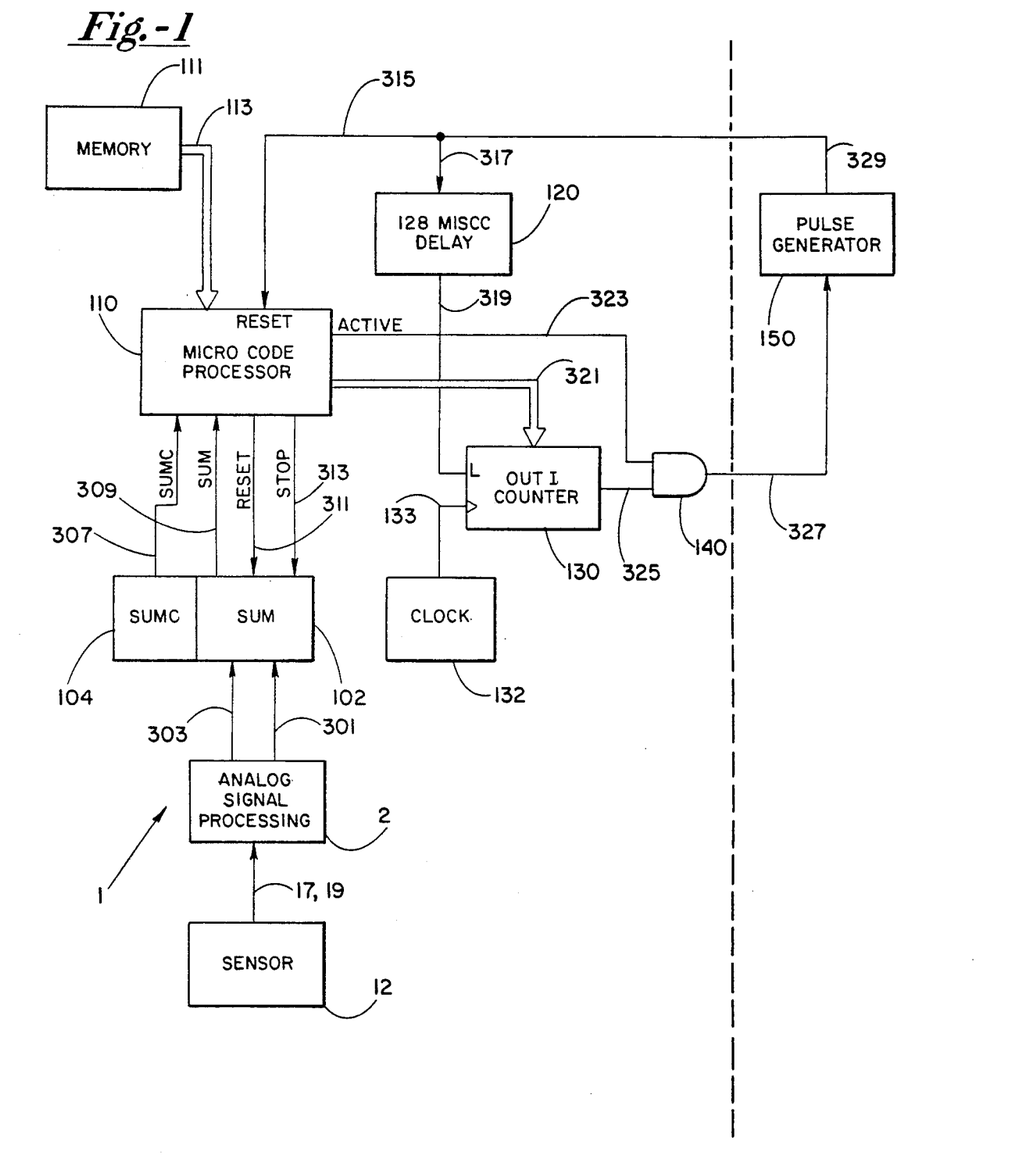
FIG. 1 is a block diagram of a cardiac pacemaker as provided by one embodiment of the invention.

Referring now to FIG. 1, a block diagram of a cardiac pacemaker as provided by one embodiment of the invention is shown. While it is deemed helpful to the understanding of the invention to describe it in terms of an application in a cardiac pacemaker, it is not intended to be so limited. Those skilled in the art will recognize other applications as uses for the invention in areas where low noise signal conditioning of low level, low frequency signals is advantageous. The pacemaker 1 includes a sensor 12, an analog signal processing section 2, a first means for summing 102, a second means for summing 104, a microcode processing means 110, a memory means 111, a delay means 120, a means for counting 130, a first clock 132, logical AND gate means 140, and a means for generating stimulation pulses 150. The analog section 2 is coupled to the first summing means 102 by means of lines 303 and 301. First and second summing means 102 and 104 share counting signals and are connected to microcode processor by means of SUMC signal line 307, SUM signal line 309, RESET signal line 311, and STOP signal line 313. The pulse generator 150 is coupled to the microcode processor 110 by means of line 329 and branch line 315. Line 329 is also connected to the delay means 120 by line 317. The delay means 120 is connected to the latching input of OUTI counter 130 by line 319. Clock 132 is connected to the clock input of OUT counter 130 by line 133. Memory means 111 is coupled by bus 113 to the microcode processor 110. Microcode processor 110 supplies data to OUTI counter 130 by means of bus 321. ANDgate 140 receives an output signal from the counter on line 325 and an ACTIVE signal from the microcode processor on line 323 and outputs a logical AND function of those two signals to pulse generator 150 on line 327.

The memory means 111 is advantageously used to store parameters which may be preset by a physician and may, as a result, vary from patient to patient. Such parameters include a response factor (RESP) which, in one example embodiment of the invention, varies from 0.5 to 4 in 16 logarithmic steps.

The RESP factor is available to allow a physician to compensate for individual patients in which a pacemaker is implanted. For example, in an older individual, a small movement may require a greater increase in heart rate than the same movement in an athlete. However, a small movement will generate a small value for the sensor rectified average (SRA) because an older individual will not tend to move very rapidly. Since a large increase in heart rate is required for an older patient, a larger factor will be used to multiply up the change in rate for a given SRA. A base rate representing a minimum rate limit is also programmable by the physician. The physician may, in one example, select one of 16 preprogrammed rates as a base rate, where the 16 preprogrammed rates vary from 30 to 120 beats per minute. A maximum sensor rate (MSR) may also be stored in memory to serve as an upper limit on the pulse generator output.

Figure 2:
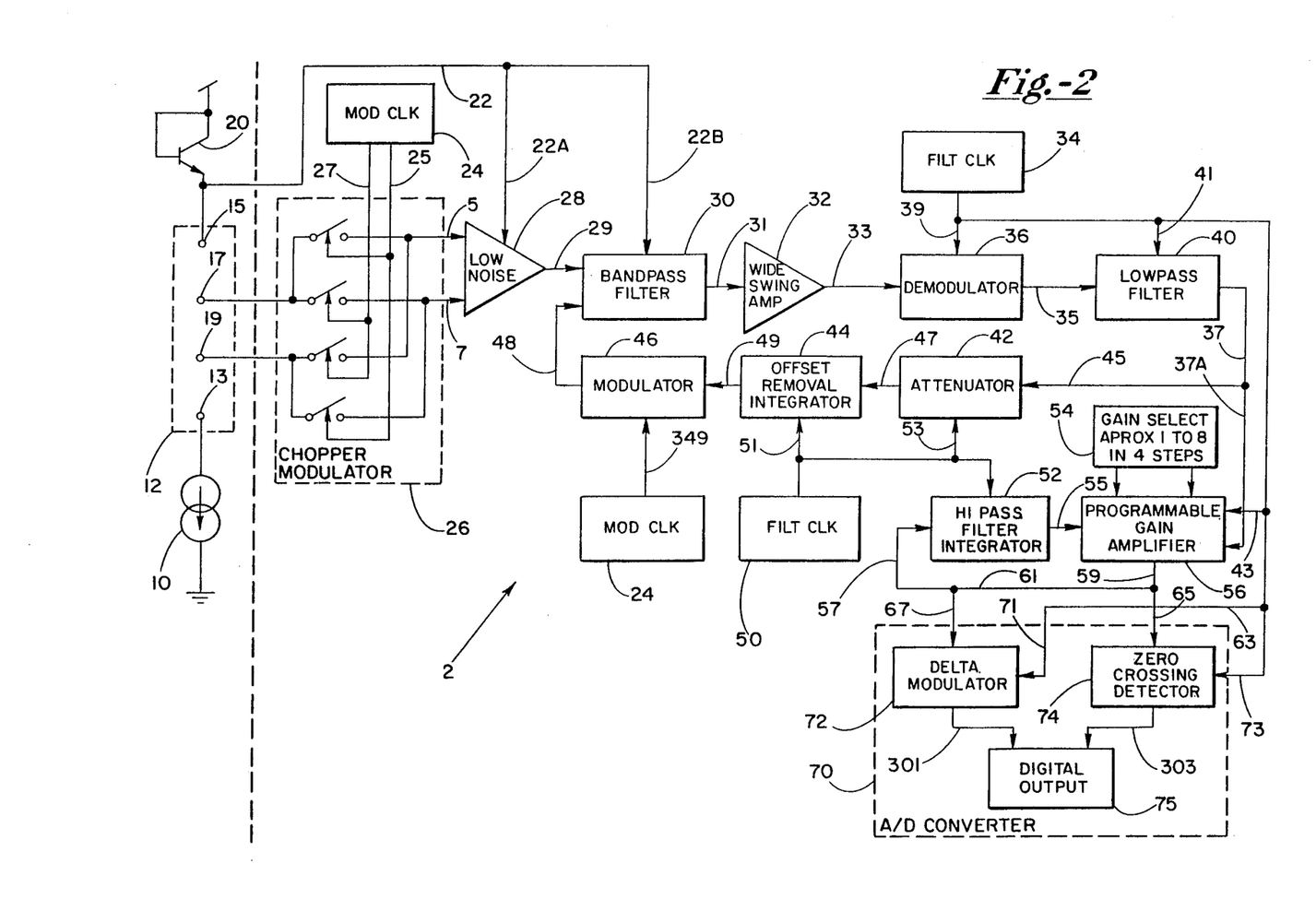
FIG. 2 is a block diagram of an analog signal processing network as employed in one embodiment of the invention.

Referring now to FIG. 2 the analog section 2 of the pacemaker of the invention is shown in a more detailed block diagram. The analog signal processing section is connected to a means for sensing acceleration 12 having programmable DC excitation current source 10 connected to a first excitation input 13 and a means for level shifting 20 connected to a second input 15.

In one example embodiment of the invention, the programmable DC excitation current means advantageously operates in approximately 4.7 microamp increments in 4 steps. The level shifting means 20 advantageously provides about a 0.5 volt level shift to the sensor 12. The sensor means 12 may advantageously be an integrated circuit accelerometer bonded in a leadless chip carrier. The accelerometer may advantageously include a balanced bridge that changes resistance in proportion to acceleration in the ±2g range, perpendicular to the bonded surface, at frequencies from DC to 350 Hz. The accelerometer bridge may include a source resistance of about 3.5K ohms to 6.5K ohms. Such accelerometers are known in the art and are commercially available.

The sensor 12 provides first and second output signals 17, 19 to a means for chopping and modulating 26. Chopper modulator means 26 has first and second clock inputs 27 and 25 connected to a modulator clock 24. In one embodiment of the invention, the modulator clock operates at about 2.73 KHz. A first amplifier means 28 has first and second inputs 5 and 7 connected to first and second outputs of the chopper modulator means 26 and further has an output 29 connected to a means for filtering 30. In one example embodiment, the first amplifier means 28 is a low noise preamp having a gain of about 7. The filtering means 30 is advantageously a band pass filter. In one example, the filtering means 30 advantageously comprises a fourth order filter having a gain of about 9 and a frequency band of about 300 Hz to about 8000 Hz. The level shifting means 20 is further connected by means of line 22 to a third input 22A of the amplifier means 28 and a level shifting input 22B of the band pass filtering means 30. The band pass filtering means also has a second input 48 and an output 31. A second amplifier 32 is connected to the output of the band pass filter means 30 by means of a line 31. In one example embodiment of the invention, the second amplifier means has a gain of about 5 and comprises a wide swing amplifier. The second amplifier means has an output signal 33 which is coupled to a means for demodulating 36. Demodulating means 36 includes a clock input 39 connected to a first filter clock 34. The first filter clock advantageously operates at about 2.73 KHz. Circuit elements 24, 28, 30 and 36 operate to condition and amplify the sensor signal.

The demodulator output 35 is coupled to a low pass filter means 40 which also has a clock input 41 connected to the filter clock 34. The low pass filter means 40 has an output 37 which is connected by means of a line 45 to means for attenuation 42. Attenuation means 42 includes an output 47 connected to a means for offset removal integration means 44. The offset removal integration means includes an output connected by a line 49 to a modulation means 46. The attenuation means 42 and integrator means 44 each have clock inputs 51, 53 connected to a second filter clock 50. In one example embodiment, the second filter clock operates at about 683 Hz. Modulation means 46 has a clock input 349 connected to modulator clock 24. The modulation means 46 further has an output 48 connected to the second input of band pass filter means 30.

The low pass filter means 40 is further connected by means of line 37A to a first input of a programmable gain amplifier means 56. The programmable gain amplifier means 56 further has a clock input at 43 which is also connected to the first filter clock 34. Means for high pass filter integration 52 has an input 57 and an output 55 connected to the programmable gain amplifier at a second input. The programmable gain amplifier also includes an output 59 which is coupled by line 61 to input 57 of the high pass filter integrator. An analog-to-digital converter section 73 comprises a delta modulator 72, a zero crossing detector 74 and a digital output circuit 75. The delta modulator includes a clock input 71 connected to filter clock 34 and a first signal input 67. The zero crossing detector means 74 includes a clock input 73 connected to the filter clock 34 and a signal input 65. The delta modulator 72 outputs a signal on line 301 and the zero crossing detector 74 outputs a signal on line 303 to the digital output means 75.

Figure 4:
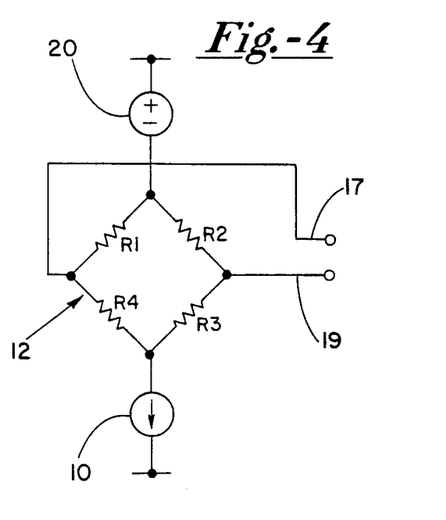
FIG. 4 is a more detailed schematic diagram of the bridge section of an accelerometer as employed in one embodiment of the invention.

Having described the configuration of the elements in the analog section, it will now prove helpful to the understanding of the invention to explain the operation of the analog section as implemented in one example embodiment of the invention. It will be understood that this example is by way of explanation and not limitation of the invention. Still referring to FIG. 2, in one example of the invention, the sensor means 12 is excited by the patient's motion which results in passing a current through the bridge section shown in detail in FIG. 4 comprising resistors R1, R2, R3 and R4. A differential acceleration signal is produced across the bridge and is offset by a diode drop of about 0.5 volts by the level shifter 20 to move the signal into the operating range of the analog section 2. The signal at the sensor output is approximately 30 microvolts peak-to-peak/g riding on the 0.5 volt offset and is referred to as the Raw Accelerometer Output (RAO). The expected voltage sensitivity at the bridge terminals 17 and 19 is about 30 microvolts per g of acceleration. The output signal transmitted to the chopper modulator 26 ranges in frequency from DC up to about 350 Hz. The chopper modulator means 26 translates those frequencies up to about 2.73 KHz by the modulation process using the modulator clock 24. Gain is added to the signal by amplifier means 28 which is preferably a low noise preamplifier with a gain of about 7. The band pass filter 30 then receives the amplified signal on line 29 and adds another gain of about 9. The second amplifier means 32 adds still another gain of about 9 to the signal before passing it to the demodulator 36. The band pass filter 30 is used for providing noise rejection of the chopper amplifier 26. This is required because the modulator 26 creates harmonics other than the chopper frequency which occur at integral multipliers of the chopper frequencies. The band pass filter 30 selects only those frequencies which have the best signal-to-noise ratio with frequencies in the range of about 300 to 8,000 Hertz. After the initial modulation, amplification and filtering, the signal is transmitted on line 33 to the demodulator means 36. In one example embodiment, the signal is demodulated with a carrier of approximately 3 KHz. The demodulator 36 operates to demodulate the signal down to DC at output line 35. Any DC signal changes at the sensor are now present at the output of the demodulator. The demodulator does not operate to band limit the signal, therefore, the bandwidth is primarily limited by the sensor 12 up to this point in the circuit. That is, it ranges in frequency from about 0 to about 300 Hz. On line 35, the signal has the same morphology as at the output of the sensor, however, the signal is increased in amplitude since it has been amplified. The amplifier stages initially receive about ⅓ of a microvolt input with reference to the RMS noise level. This allows the circuit to distinguish about 1/100 of a g and determine that it is something other than the system noise.

In one example embodiment of the invention, the low pass filter 40 limits the highest frequencies of the system to about 10 Hz. At line 37, therefore, the signal frequency ranges from DC to 10 Hz. The low pass filter in one embodiment of the invention advantageously adds a gain of about 2 to the signal. The overall gain of the system is controlled by the programmable gain amplifier 56. In one embodiment of the invention, the programmable gain amplifier has 4 different settings. Relative settings of 1, 2, 4 or 8 may be selected through the gain select means 54. It is also possible to omit the programmable gain selection feature and, instead, fix the system gain to a pre-determined value.

The programmable gain amplifier means 56 and the high pass filter integration means 52 operate together to form a feedback loop which performs as a high pass filter. The high pass filter integration means 52 operates at a frequency of about 1.0 Hz. This feedback loop operates to eliminate DC signals. The bandwidth of the signal transmitted to the analog-to-digital converter 73 is thereby band limited to between 1 and 10 Hz. Attenuation means 42, offset removal integration means 44 and modulator 46 operate to provide a second feedback loop. This loop suppresses input signals that contain a large DC component which may be caused by DC errors in the accelerometer sensor 12 caused, in turn, by gravity or unbalanced bridges. The second feedback loop operates at a frequency of about 0.2 Hz. The second feedback loop feeds back the signal into a second input of the band pass filter having a gain of about 0.01. Essentially, the DC signal is reduced in amplitude and integrated through the second feedback loop. Because the band pass filter is operating at an RF frequency, that RF signal must be converted back up to the RF range with the modulator 46. After that, it is injected back into the band pass filter at line 48. The DC removal loop comprising the attenuater 42, offset removal integrator 44 and modulator 46 operates at the front end of the analog section enabling suppression of DC signals before any amplifier reaches saturation. Therefore, the analog section can tolerate large DC components in the input signal at lines 17 and 19.

The second feedback loop comprising elements 42, 44 and 46 most particularly operates to remove instantaneous changes, as when the patient changes his body position in the earth field. For example, if the patient is lying on his back and rolls over to lie on his chest, the high pass filter 52 will remove the instantaneous change and the low pass filter 40 will recenter the operation of the front end amplifier 28 so that it is still capable of recognizing small signals. The sensor 12 is essentially DC and every different orientation in the field yields a different sensor output. Some such changes in orientation are usable signals.

The delta modulator means 72, zero crossing detector 74 and digital output means 75 operate together to form an analog-to-digital converter. The zero crossing detector 74 supplies signal rectification information by recognizing when the output signal crosses zero. At every zero crossing the delta modulator is purged of cumulative errors that may have been built up. Essentially, the handoff between the analog and digital section comprises (1) zero crossings which are used to provide rectification and error removal in the delta modulator and (2) the delta modulator data stream. The delta modulator 72 and zero crossing detector 74 may be constructed according to means well known in the art. The delta modulator provides fixed increments to the digital section. The delta modulator includes a tracking integrator which either increases or decreases by a fixed amount, based on a comparison between the integrator output and the input signal at line 67. For example, if the input at line 67 is greater than the integrator output at line 55, a "1" is produced in the delta modulator bit. The logical "1" then increases the integrator value by one least significant bit (LSB). It keeps adding or subtracting one LSB or one count to track the input signal. Each time the signal increases, the delta modulator generates a "1" and each time the signal is decreasing the delta modulator generates a "0". The bits are then counted over a predetermined interval to establish the value of the analog-to-digital converter. The second half of the analog-to-digital conversion occurs in the digital output section where the counting is accomplished.

The RAO is amplified by a programmable gain of 1000-8000 through the above-described circuitry and filtered by the programmable filter 56 with a nominal low pass of about 1 Hz and high pass at about 10 Hz. At output 59, the acceleration is approximately 600 Mv/g times the signal. This is referred to as the filtered accelerometer output (FAO). The FAO is digitized by means of the switched capacitor delta modulator circuit 72 sampling at a frequency of about 2738 Hz with a slew rate of about 9 mv. The deltas are rectified and counted by a 6 bit up/down counter at the same frequency, counter 102 yielding a range of 0-576 Mv. Because of the rectification, only 0-300 Mv of the range is used. The counter is constructed so that it will not roll over or under. In addition, the up/down counter is reset when FAO crosses zero to keep the delta modulator from counting to the maximum or minimum value because of normal digitizing errors and offsets. The 6 bit value is passed to the SUM counter and is referred to as the Delta Modulator Output (DMO) at line 301.

Figure 5:
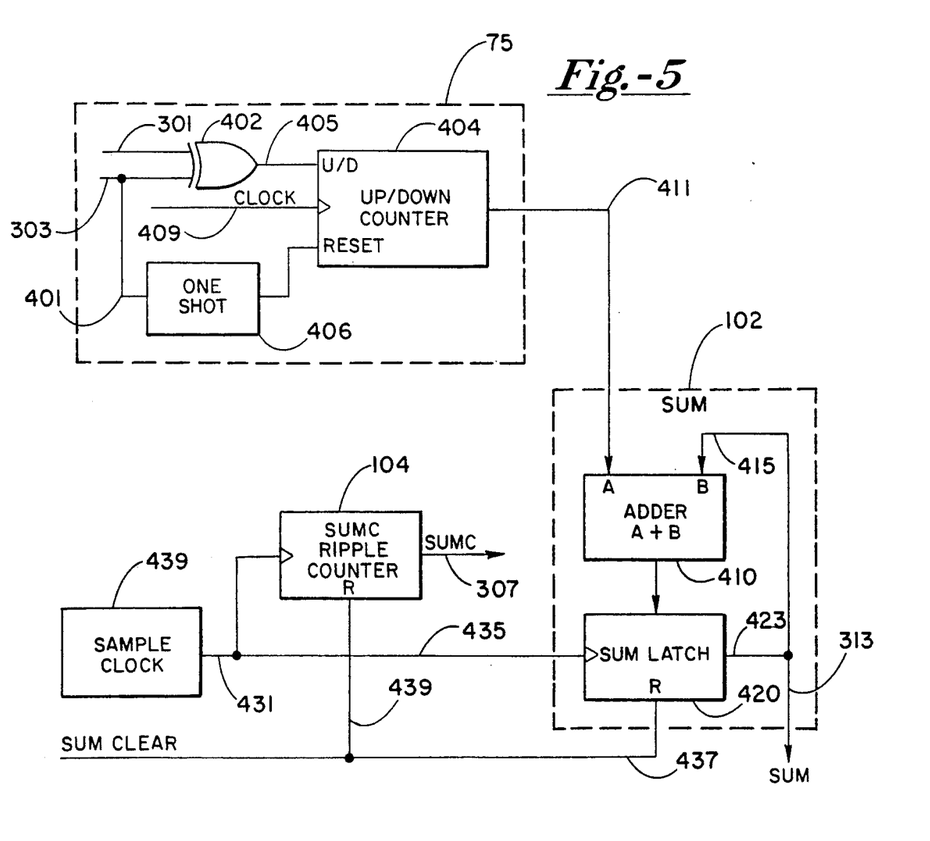
FIG. 5 is a more detailed schematic diagram of a portion of the sampling devices employed in one embodiment of the invention.

Referring now to FIG. 5, a more detailed block diagram of the digital output section 75 and summing sections 102, 104 of the digital section of the pacemaker are shown. An exclusive ORgate 402, a one-shot 406, and an up/down counter 404 comprise the digital output section 75. An adder 410 and a SUM latch 420 comprise the first counting means 102. The second counting means 104 is comprised of ripple counter 104. Delta modulator 72 provides a delta modulator signal on line 301 to one input of the exclusive ORgate 402. Zero crossing detector 74 provides a zero crossing signal on line 303 to a second input 403 of exclusive ORgate 402. Zero crossing detector also provides the zero crossing signal on input 401 of one shot 406 which is used to reset the up/down counter 404 by dividing the pulse on line 407. The up/down counter is operated at clock input 409 at a rate of about 2.7 KHz. The exclusive ORgate 409 provides a counting signal to the up/down counting input on line 405. The counter provides the delta modulator output on output 411 to the A input of adder 410. The output of adder 410 is routed on line 313 to the microrode processor 110 and on line 415 to the B input of adder 410. SUM latch 420 continues to accumulate the SUM until a reset pulse is received at line 437 from the microcode processor. Similarly, the SUMC counter is reset when a reset pulse from the microcode processor is received on the reset input on line 439. Both the SUM accumulator and the SUMC counter are advantageously operated at about an 85 Hz rate which is provided on line 431 and routed to SUMC on line 433 and SUM 102 on lines 435. In one example embodiment of the invention, the SUMC counter is advantageously an 8 bit ripple counter. A sample clock 439 controls the sampling rate of the SUM and SUMC counters. In one example embodiment, the SUM accumulator samples DMO every 11.72 msec (85 Hz) and adds the new DMO value to itself according to the equation: SUM=-SUM+DMO. The SUM accumulator will continue to add the DMO values to itself during each cardiac cycle. SUMC 104, counts the number of samples SUM during the cardiac cycle. At the end of the cardiac cycle, SUM will range from 0 to 8192 (13 bits) and SUMC will range from 30 to 170 (8 bits). Every cardiac cycle, the microcode reads SUM and divides by SUMC according to the equation:

$$SRA = SUM \div SUMC.$$

The final result is called the Sensor Rectified Average (SRA). Because of the rectification described hereinabove and the energy function to be described below, only 10% of the range is used. The SUM is multiplied by 8 to move the SRA into a full dynamic range.

After SRA is formed, SUM and SUMC are reset and the summing and dividing cycle repeats. SRA range from 0, representing no activity, to 255 representing maximum activity. If SRA is calculated to be greater than 255, the microcode will force it to equal 255. A programmable option may advantageously be provided to even out the summing times between fast pacing rates and slow pacing rates. If the pacing rate is faster than 512 msec., another cycle or two will be averaged before the microcode reads SUMC and SUM.

Because of noise or low level activity that may be sensed bu the accelerometer, a Sensor Average Threshold (SAT) is advantageously included as programmable to ignore such unwanted values. This is done by subtracting SAT from SRA to give an Offset Sensor Rectified Average (OSRA). Once a number that represents the offset rectified average is produced, a Sensor Determined Interval (SDI) is formed using the Response Number (RESP) and subtracting it from the programmed rate parameter. OSRA is used with the programmable sensor response multiplier to form a sensor determined delta (SDD) which is rate in pulses per minute (PPM). The SDD is added to the programmed rate and the result is limited to the maximum sensor rate (MSR). After this step, the number is converted to the interval sensor determined interval (SDI) (where Interval=60,000/ppm). SDI advantageously ranges from 255 (which corresponds to 30 ppm) to 45 (which corresponds to 170 ppm) and changes every cycle with activity. SDI is compared with the actual pacing interval (API), to determine the response of the pulse generator. In simplified pairs, the algorithm can be thought of in three phases as follows: (1) if API is greater than SDI then the pacing interval is increased, but limited to SDI; (2) if API equals SDI then there is no change in the interval; (3) if API is less than SDI, then the interval is increased but limited to the sensor recovery number.

Figure 3A:
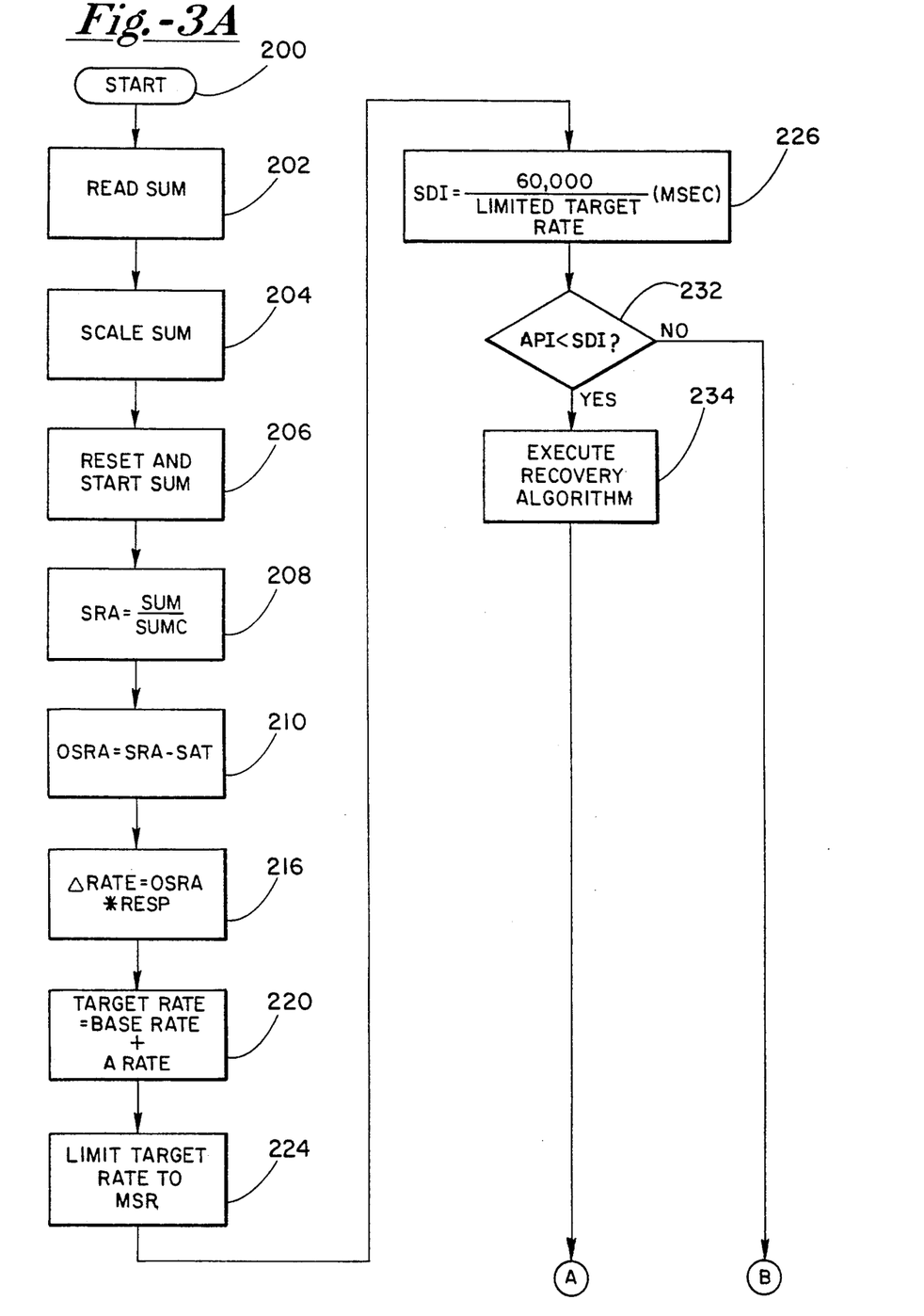
FIGS. 3A and 3B are intended to be read as one figure when pieced together showing a flow diagram of one example of a method as employed in the invention.
Figure 3B:
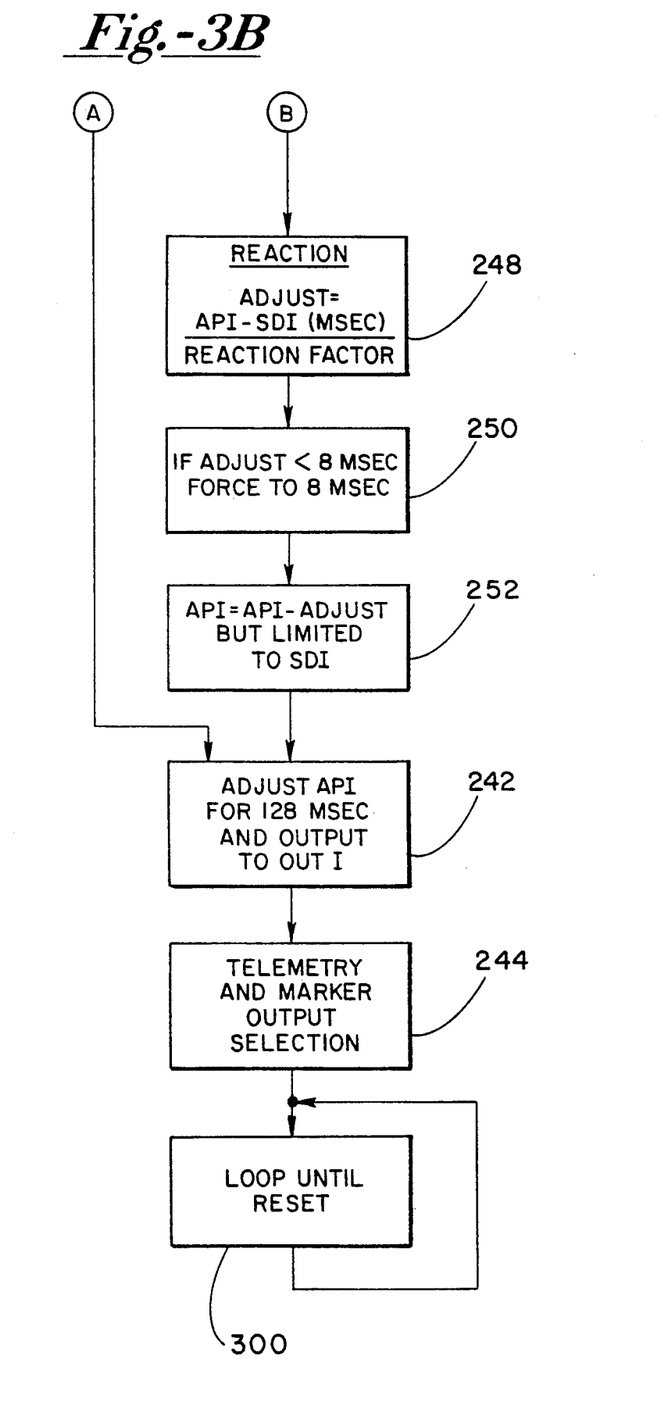

Now referring to FIGS. 3A and 3B, a flow diagram of the microcode contained in the microcode processor is shown. The process begins at step 200 and continues to step 202 where the SUM accumulator is stopped and read. At step 204 the value for SUM read at step 202 is scaled. That is, since the value read is an average absolute value as opposed to a peak-to-peak value, it must be scaled upwards to optimize the dynamic range. At step 206, the SUM accumulator is reset and restarted. At step 208, the SRA value is determined by dividing SUM by the value in accumulator SUCM. At step 210 the offset sensor rectified average OSRA is determined according to the method described hereinabove. The process then continues on to step 216 where a response factor (RESP) is applied to SRA to yield a change in rate called ΔRATE At step 220, the target rate is calculated as the base rate value from a lookup table in memory added to ΔRATE. The target rate is limited to MSR by a comparison performed at step 224. The SDI value is then determined in milliseconds at step 226 as 60,000 divided by the limited target rate. The process continues to step 232 where SDI and API are compared. The first time through the algorithm an initial API value is set equal to the inverse of the base rate. If API is less than SDI, the process is routed to step 234. If API is greater than or equal to SDI, the process is routed to step 248. If it is not, the process proceeds to step 234 which executes a recovery algorithm in accordance with well known recovery methods, such as taught by U.S. Pat. No. 4,940,052. The process then continues to step 242 where API is adjusted for 128 msec and output to the OUTI counter. Note that the 128 msec adjustment serves to account for the calculation time necessary to run the microcode algorithm. In effect, this adjustment removes a 128 msec offset from the start of a cardiac event caused by the time it takes to calculate the new API or actual pulsing interval. The 128 msec adjustment to API is advantageously accomplished by delay means 120. At step 244, telemetry and marker output selections are made in a conventional manner. At step 246 a cycle/SUM routine is entered and the process continues to step 300 to await the next standard logic chip reset pulse.

If step 248 is entered, a reaction algorithm sets an adjust value equal to API minus SDI over a preselected reaction factor. The reaction factor is selected so as to avoid sudden large increases in heart rate. The process checks the adjust factor at step 250 and if it is less than 8 msec it is forced to 8 msec. API is then set equal to API minus the adjust value but limited to SDI at step 252. The process then proceeds as before to step 242.

Referring again to FIG. 1, the adjusted and limited API value is clocked into the OUTI counter 130 on bus 321. When the ACTIVE line 323 is high, the adjusted and limited API value is transmitted through gate 140 into the pulse generator which outputs stimulating pulses to electrodes (not shown) attached to the patient. The stimulating pulses so generated are at the rate inversely proportional to the adjusted API value.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A rate adaptive pacemaker comprising:
   means for sensing a physiological parameter wherein the sensing means provides an output signal corresponding to the sensed physiological parameter;
   means for providing a sensor determined interval from the output signal coupled to the sensing means and comprising means for performing analog signal processing and means for performing digital signal processing;
   means for determining an actual pacing interval;
   means for determining a pacing rate coupled to the means for providing the sensor determined interval and the means for determining the actual pacing interval wherein the pacing rate is a function of both the sensor determined interval and the actual pacing interval;
   means for generating pacing pulses at said pacing rate; and
   wherein the means for performing analog signal processing compromises:
   (a) means connected to receive the output signal for chopping and modulating the output signal and providing a first modulated signal;
   (b) first means for amplifying coupled to the chopping and modulating means to receive the first modulated signal and provide a first amplified output;
   (c) first means for filtering having a first input coupled to receive the first amplified output and providing a first filtered output;
   (d) second means for amplifying coupled to the first filtered output and providing a second amplified output;
   (e) demodulator means for demodulating having an input coupled to the second amplified output and providing a demodulated output;
   (f) second means for filtering having an input coupled to the demodulated output and providing a second filtered output;
   (g) third means for amplifying having a first input also coupled to the second filtered output and providing a third amplified output; and
   (h) means for converting analog signals to digital signals having first and second inputs coupled to the third amplified output.

2. The pacemaker of claim 1 wherein the means for sensing a physiological parameter comprises an accelerometer.

3. The pacemaker of claim 1 further comprising means for programming a gain of the third amplifying means.

4. The pacemaker of claim 1 wherein the first filtering means comprises a band pass filter having a bandwidth ranging from about 300 Hz to 8000 Hz.

5. The pacemaker of claim 1 wherein the analog-to-digital conversion means comprises a delta modulator coupled to the first input providing fixed increments to said means for performing digital signal processing and a zero crossing detector coupled at the said input supplying signal rectification information to said means for performing digital signal processing.

6. The pacemaker as specified in claim 1 further comprising:
   (i) feedback means for suppressing DC signals having an input coupled to the second filtered output.

7. The pacemaker of claim 6 wherein the feedback means comprises:
   (a) means for attenuation having an input coupled to the second filtered and having an attenuated output;
   (b) means for removing offset signals having an input coupled to the attenuated output and having an offset removal output; and
   (c) means for modulating having an input coupled to the offset removal output and having an output coupled to the second input of the first filtering means.

8. The pacemaker of claim 7 wherein the analog-to-digital conversion means comprises a delta modulator coupled to the first input providing fixed increments to said means for performing digital signal processing and a zero crossing detector coupled at the second input supplying signal rectification information to said means for performing digital signal processing.

9. The pacemaker as specified in claim 6 further comprising:
   (j) means for filtering and integrating DC signals having an input coupled to the third amplifier output.

10. The pacemaker as specified in claim 1 wherein the means for determining the pacing rate further comprises means for increasing the pacing rate when the actual pacing interval is less than the sensor pacing interval, means for maintaining the pacing rate when the actual pacing interval is less than the sensor pacing interval, and means for decreasing the pacing rate when the actual pacing interval is less than the sensor pacing interval.

11. A method for operating a cardiac pacemaker implanted in a patient's body comprising the steps of:
   (a) sensing acceleration of the patient's body;
   (b) providing an acceleration output signal proportional to the sensed acceleration;
   (c) band limiting and filtering the acceleration output signal to provide a filtered accelerator output;
   (d) digitizing the filtered accelerator output;
   (e) sampling the filtered accelerator output and summing the samples over a cardiac cycle to provide an accumulated sum;

(f) determining a sensor rectified average proportional to the accumulated sum divided by the number of samples in a cardiac cycle;
(g) determining a sensor determined interval proportional to the sensor rectified average;
(h) determining a pacing rate based in part on the sensor determined interval; and
(i) generating pulses at the pacing rate.

12. The method of claim 11 wherein the step for determining a pacing rate, further comprises the steps of:
   (a) determining an actual pacing interval;
   (b) comparing the actual pacing interval with the sensor determined interval;
   (c) executing a recovery algorithm if the actual pacing interval is less than the sensor determined interval; and
   (d) executing a reaction algorithm if the actual pacing interval is greater than or equal to the sensor determined interval.

13. The method of claim 12 wherein the step of executing a reaction algorithm comprise the steps of:
   (a) determining an adjustment factor proportional to the difference between the actual pacing interval and the sensor determined interval;
   (b) adjusting the actual pacing interval by applying the adjustment factor to provide an adjusted actual pacing interval;
   (c) compensating the adjusted actual pacing interval for processing time delays; and
   (d) outputting the adjusted and compensated actual pacing interval as the pacing rate to the cardiac pacemaker.

* * * * *